United States Patent [19]

Knoepfler

[11] Patent Number: 5,273,531
[45] Date of Patent: Dec. 28, 1993

[54] METHOD OF APPLYING THROMBIC POWDER IN LAPAROSCOPIC PROCEDURES

[76] Inventor: Dennis J. Knoepfler, 1383 Whitaker La., Amelia, Ohio 45102

[21] Appl. No.: 948,187

[22] Filed: Sep. 21, 1992

[51] Int. Cl.$^5$ .............................................. A61M 5/00
[52] U.S. Cl. ...................................... 604/58; 604/212
[58] Field of Search .............................. 604/57–60, 604/212, 213, 215, 216; 606/92, 93

[56] References Cited

U.S. PATENT DOCUMENTS

| | | | |
|---|---|---|---|
| 39,678 | 8/1863 | Russell | 604/58 |
| 170,182 | 11/1875 | Molesworth . | |
| 471,865 | 3/1892 | Howard . | |
| 566,411 | 8/1896 | Schoene | 604/58 |
| 576,437 | 2/1897 | Elliot | 604/58 |
| 693,587 | 2/1902 | Campbell . | |
| 1,022,601 | 4/1912 | Rumberg et al. . | |
| 1,114,114 | 10/1914 | Cochenour . | |
| 1,145,520 | 7/1915 | Smith . | |
| 1,685,280 | 9/1928 | Findley | 604/58 |
| 1,934,793 | 11/1933 | Crain et al. . | |
| 2,151,418 | 3/1939 | Bolté | 604/58 |
| 2,223,611 | 12/1940 | Gross | 604/58 |
| 2,307,986 | 1/1943 | Bolté et al. | 604/58 |
| 2,507,702 | 5/1950 | Fields . | |
| 2,519,555 | 8/1950 | Fields | 604/58 |
| 4,017,007 | 4/1977 | Riccio | 604/58 |
| 4,210,140 | 7/1980 | James et al. | 604/58 |
| 4,620,847 | 11/1986 | Shishov et al. | 604/58 |
| 4,790,819 | 12/1988 | Li et al. | 604/59 |
| 5,021,059 | 6/1991 | Kensey et al. | 604/60 |
| 5,129,882 | 7/1992 | Weldon et al. | 604/53 |

FOREIGN PATENT DOCUMENTS

| | | | |
|---|---|---|---|
| 15244 | 9/1897 | Switzerland | 604/58 |
| 10563 | of 1896 | United Kingdom | 604/58 |

OTHER PUBLICATIONS

Endo-Avitene ™—Advertising brochure, Med Chem Products, Inc. Woburn, Mass. 01801—no date.
C. J. Decker: An Efficient Method For The Application of Avitene Hemostatic Agent; Surgery, Jun. 1991, Gynecology & Obstetrics, vol. 172, No. 6., p. 489.

*Primary Examiner*—Ralph Lewis
*Attorney, Agent, or Firm*—Gregory J. Lunn

[57] ABSTRACT

An apparatus to force powdered agent, such as a thrombic agent, into the operative site of a laparoscopic procedure includes an elongated tube, a powder chamber and a mechanism to force the powder through the tube. Generally, this mechanism will be a source of pressurized air such as an air bulb, a syringe or a tank or cartridge of gas. In an alternate embodiment, the chamber can receive a tubular capsule full of the powder which is open at both ends so that air forced through the tube will force powder in the capsule through the tube and into the operative site.

12 Claims, 1 Drawing Sheet

METHOD OF APPLYING THROMBIC POWDER IN LAPAROSCOPIC PROCEDURES

BACKGROUND OF THE INVENTION

Thrombic agents are designed to be topically applied to a bleeding area to control and stop the bleeding. There are many different types of these. One particular type is a microfibular collagen hemostat. A well known microfibular collagen hemostat is Avitene TM sold by Medchem. This is 100% collagen. It is particularly useful in surgical procedures. This product is available in sheets and powder form.

When the operative procedure is an open procedure, the powder can be used by simply spreading it over the area. But in a laparoscopic procedure, this will not work. For scopic procedures, the makers of Avitene TM recommend a relatively complex procedure where small sheets of the Avitene TM are grasped by a nonlocking forceps and inserted through a trocar and applied to the area. This is time consuming. The hemostat sheet must be cut to the desired size, wrapped around the forceps in a manner that will permit them to be inserted through the cannula into the operative site.

SUMMARY OF THE INVENTION

Accordingly, it is an object of the present invention to provide an apparatus for applying hemostat powder to an operative site in a scopic procedure. Further, it is an object of the present invention to provide a method to impel this powder directly on the operative site and to do so quickly and easily in a precisely desired area.

The objects and advantages of the present invention are provided by using a tubular propulsion device that is adapted to be fit through a cannula to the operative site wherein the device incorporates a chamber adapted to receive the powder and a means to impel this powder through the tube into the operative site.

The powder can be introduced into the tube through an enlarged chamber which has a door adapted to permit the powder to be placed inside the tube and to be shut to prevent gas leaks. Alternately, the device can include an opening to receive a capsule containing the powdered product. Preferably the powder is gas propelled into the operative site. The propelling gas can be emitted from a rubber bulb or syringe. Alternately, a mechanical actuating device can be used to force powder through the tube using gas from a supply source.

The capsule itself has a rigid tubular exterior and a forward and rear frangible cover with the powder in between. The frangible cover can be forced by gas or physical means to rupture, allowing the powder to escape and be forced through the tube. In a preferred embodiment, the frangible cover is either a very thin foil or a sheet of the thrombic material itself.

The objects and advantages of the present invention will be further appreciated in light of the following detailed description and drawings in which:

DETAILED DESCRIPTION

Figure 1:
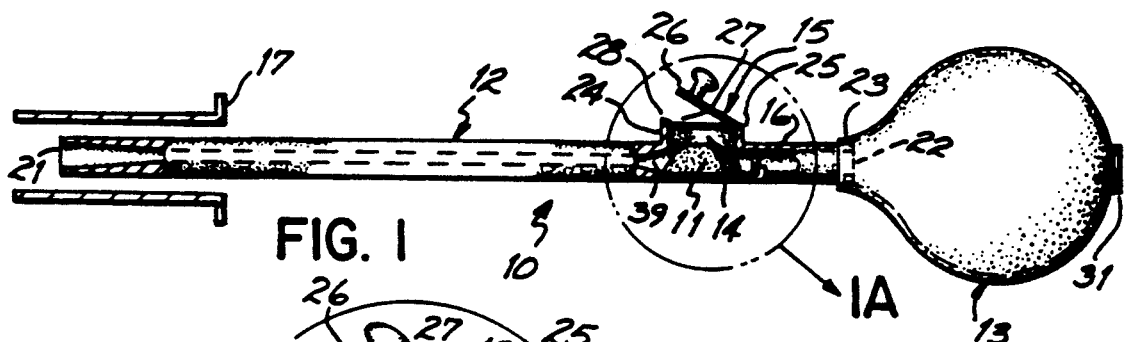
FIG. 1 is a side elevational view partially in cross section of a first embodiment of the present invention.

As shown in FIG. 1, the present invention is a powder dispenser 10 primarily adapted to dispense thrombic powder 11 in a laparoscopic procedure. As such, the dispenser 10 includes an elongated tube 12, a bulb 13, a powder chamber 14 which is accessible through lid 15. Between the powder chamber 14 and the bulb 13 is a one-way valve 16.

More particularly, tube 12, which is shown being inserted through a cannula 17, includes a first end 21 as shown and a distal second end 22. Second end 22 is inserted into the opening 23 of rubber bulb 13 to thereby form a seal between the exterior wall of tube 12 and the interior surface of the opening 23 of bulb 13.

The powder chamber 14 includes a rectangular peripheral wall 24. Lid 15 to the powder chamber 14 is attached to wall 24 along living hinge 25. An opposite edge 26 of lid 15 is adapted to snap-fit into a groove 27 under a latch 28 which extends above wall 24. This holds the lid 15 in position on the upper edges of wall 24 sealing chamber 14. Alternately, the chamber 14 could be round with exterior threads and lid 15 could be a round screwed-on lid. The chamber tapers as it joins tube wall 39.

Figure 1A:
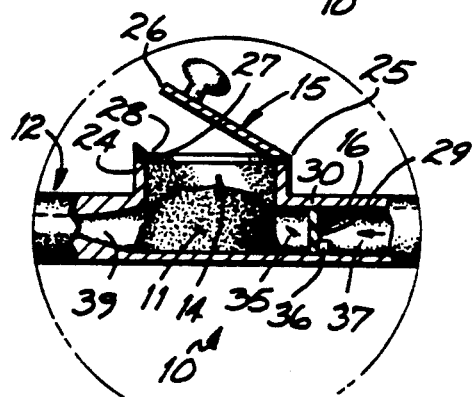
FIG. 1a is an enlarged cross sectional view of the circled 1a—1a portion of FIG. 1.

As shown further in FIG. 1a, upstream of powder chamber 14 is one-way valve 16. One-way valve 16 is simply a rubber flap 29 which is attached along one edge 30 to the inside wall 39 of tube 12. This permits the flap 29 to raise in the direction shown by arrow 35. Upstream of flap 29 is a small annular ridge 36. At rest, flap 29 will seat on ledge 36 preventing air downstream of valve 16 from flowing back into bulb 13. The bulb 13 also includes a one-way valve 31 which allows air into bulb 13.

In use, the lid 15 of chamber 14 would be opened and powder 11 placed within chamber 14 where it rests inside tube 12 as shown in FIG. 1a. The lid would be closed with the edge 26 of lid 15 engaging the groove 27 under latch 28. This will hold the lid 15 firmly in place against wall 24 of the chamber 14. The tube 12 is then inserted through the cannula 17 into the operative site. Bulb 13 is squeezed causing air in the bulb to rush in the direction of arrow 37. This in turn causes the flap 29 to raise in the direction of arrow 35 allowing air to continue down the tube through chamber 14, forcing the powder in chamber 14 down through tube 12 onto the operative site. The internal flaring at first end 21 will encourage the entrained powder to expand as it exists the tube and spread evenly over the operative site.

Valve 31 at end of bulb 13 allows air to enter bulb 13 and the procedure can be repeated.

Figure 2:
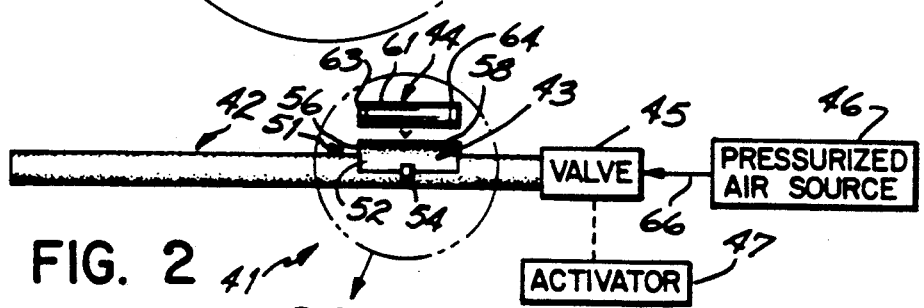
FIG. 2 is a diagrammatic view of a second embodiment of the present invention.

A first alternate embodiment of the present invention is shown in FIG. 2. In this embodiment, the dispenser 41 also includes a tube 42, a chamber 43 which is adapted to hold a capsule 44. Upstream of chamber 43 is a valve, diagrammatically shown as 45, along with an air source 46 and an activating device 47.

Figure 2A:
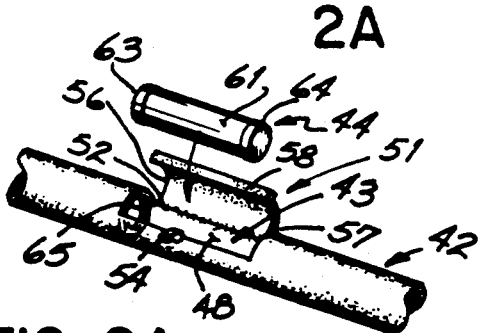
FIG. 2a is an enlarged cross sectional view of the circled portion of FIG. 2.
Figure 3:
FIG. 3 is a cross sectional configuration of a capsule adapted for use in the embodiment shown in FIG. 3.

The tube 42 is very similar to the tube shown in the embodiment of FIG. 1. However, the powder chamber 43 is significantly different. As shown in FIG. 2a, the chamber includes a chamber door 51 which is arcuate in shape exposing an opening 52 in the tube wall 48. The chamber door 51 exposes approximately one-half of the tube diameter. This permits a cylindrical capsule 44 to be inserted into tube 42. The chamber includes an annular ridge 65 which is approximately co-extensive with the downstream edge 56 of door 51.

Door 51 is attached to tube wall 48 by a living hinge 57. Opposite hinge 57 is a tab 54 which extends upward from tube wall 48 and is adapted to engage edge 58 of door 51 holding it in position.

The capsule 44 itself includes a ridged plastic or paperboard exterior tubular wall 61. Its interior is filled with loosely packed thrombic powder 62. The tubular wall 61 is open in the front and the back. The openings are covered by material 63 in the front and 64 in the back. The front and rear covers, 63 and 64 respectively, can take a variety of different forms. These can be removable material such as cellophane or foil or can be formed from material identical to the powder 62.

The pressurized air source would preferably be a source of purified nitrogen, carbon dioxide or other gas which is suitable for injection into the abdomen of the patient. The air source can be a cylinder of compressed nitrogen or carbon dioxide or alternately could be air built up in a chamber employing a pumping device. The valve and actuator can be of a variety of different designs depending on the sophistication of the use. The actuator can simply be a trigger or an electrical actuator and the valve is preferably an electric solenoid.

The device shown in FIG. 2 is used in the same manner as that in FIG. 1 with the exception of the utilization of the capsule 44. In use, the chamber door 51 would be opened, pivoted about living hinge 52 to permit the capsule 44 to be deposited into chamber 43. The capsule itself would first be prepared for use. It would be prefilled with the powder 62 and covered on the front and back with covers 63 and 64. If the cover is a plastic material or metal foil, this would first be removed prior to inserting the capsule into chamber 43. Alternately, if the front and rear covers were made of the same material of the powder, that is a thin membrane made of thrombic powder, it could be simply inserted into the chamber without removing the membrane. The capsule once inserted into the chamber 43 would be held in position by the ridge 65 engaging the capsule wall 61. The door 51 would then be closed with its edge 58 engaging tab 54 holding it in place and providing a relatively airtight seal. The activator 47 would be initiated opening valve 45 permitting a quick burst of air through tube 42 in the direction of arrow 66. This would force the powder 62 through tube 42 into the patient's abdomen. If additional thrombic powder was required, the procedure could be repeated.

Figure 4:
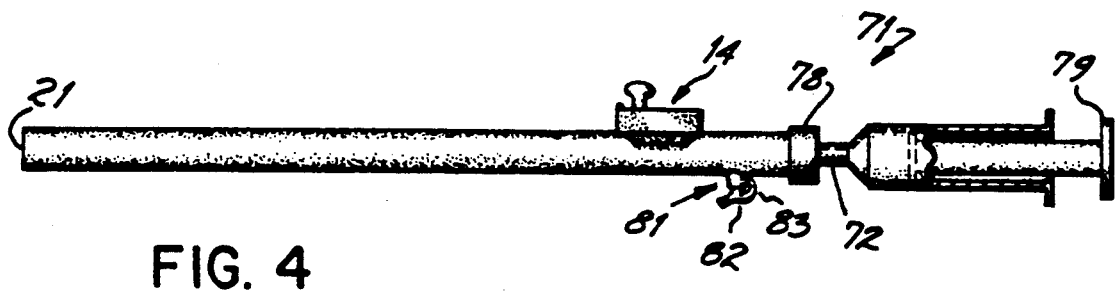
FIG. 4 is a side elevational view of another alternate embodiment of the present invention.

A third alternate embodiment is shown in FIG. 4 wherein the embodiment shown in FIG. 1 is modified and the bulb 13 replaced by a syringe 71 attached at end 72 to the upstream end 22 of tube 12. This syringe end 72 is connected to the end of the tube by a rubber connector 78. Thus, when the plunger 79 of the syringe 71 is forced inwardly, gas is forced down through the tube 12 forcing the powder 11 in the powder chamber 14 down through the tube into the patient. A one-way valve (not shown) and auxiliary air inlet 81 between powder chamber 14 and syringe 71 allow air to be drawn into the syringe 71 without drawing powder in as well. The auxiliary air inlet 81 consists of a stopper 82 and stopper strap 83. The stopper 82 plugs hole (not shown) which allows air into tube 12 for the next application of powder 11.

Thus, the apparatus and method of the present invention can be modified depending on the surgeon's preference.

The preceding has been a description of certain embodiments of the present invention. Of course there are other modifications that could be employed and yet still practice the present invention. For example, the sources of pressurized air could be changed. The valve mechanisms could be further modified. Accordingly, in light of this, the invention should be defined only by the appended claims wherein:

I claim:

1. A laparoscopic powder injector comprising a tube adapted to be inserted through a cannula for use in a scopic procedure, said tube having a first end and a second end;

means to introduce and hold powdered agent in said tube;

means to force said powdered agent through said tube and out said first end wherein said means to introduce and hold powder agent in said tube comprises a chamber open into an interior portion of said second end of said tube, said tube having a tapered portion adjacent said chamber whereby powder can be added to said chamber when said first end is inserted into said cannula wherein said means to introduce and hold powder agent in said tube comprises a capsule containing said powder having first and second ends, wherein said tube includes a port adapted to open and receive said capsule, enclose and hold said capsule in place wherein said capsule comprises a rigid tube covered at both ends with frangible sheets, said sheets comprising a thrombic agent.

2. The apparatus claimed in claim 1 wherein said means to force powder through said tube and out said first end comprises an air bulb attached to said second end adapted to force gas through said second end and force powder within said tube through said tube.

3. The apparatus claimed in claim 2 wherein said second end further includes a one-way valve to permit gas forced from said bulb only through said tube towards said first end.

4. The apparatus claimed in claim 3 further comprising a gas inlet into said second end upstream of said one-way valve to permit gas to enter from outside said tube into said bulb.

5. The apparatus claimed in claim 1 wherein said means to force said powder through said tube comprises an air source which forces air through said tube forcing said powder through said tube.

6. The apparatus claimed in claim 5 wherein said air source comprises an air bulb attached to said second end of said tube.

7. The apparatus claimed in claim 6 further comprising a one-way valve in said tube between said air tube and said means to hold powdered agent.

8. The apparatus claimed in claim 5 wherein said air source comprises a pressured air and said apparatus further comprises a valve between said means to hold powder and said pressurized air source.

9. The apparatus claimed in claim 5 wherein said air source comprises a syringe.

10. A method of introducing thrombic agent into a patient in a laparoscopic procedure comprising:

a) inserting a tube into said patient through a cannula in said patient;
b) placing powdered thrombic agent into a chamber aligned with said tube wherein said chamber is exterior said patient;
c) forcing gas through said chamber and said tube into said patient thereby forcing said powdered thrombic agent in said chamber into said patient.

11. The method claimed in claim 10 further comprising adding additional thrombic agent into said chamber with said tube remaining in said patient and forcing gas through said tube into said patient forcing said additional thrombic agent into said patient.

12. A laparoscopic powder injector comprising:

a tube adapted to be inserted through a cannula for use in a scopic procedure, said tube having a first end and a second end;

means to introduce and hold powder agent in said tube comprising a chamber and a capsule containing said powder, said capsule having first and second ends wherein said capsule comprises a rigid tube covered at both ends with frangible sheets formed from a thrombic agent and wherein said powder is a thrombic agent;

means to force said powder agent through said tube and out said end whereby additional capsules can be added to said chamber when said first end of said injector is inserted into said cannula.

* * * * *